(12) United States Patent
Morelock et al.

(10) Patent No.: US 8,734,423 B2
(45) Date of Patent: May 27, 2014

(54) METHODS AND APPARATUSES FOR TREATING TONSILS

(76) Inventors: Michael Dennis Morelock, Lakewood, WA (US); David Michael Morelock, Kenmore, WA (US)

(*) Notice: Subject to any disclaimer, the term of this patent is extended or adjusted under 35 U.S.C. 154(b) by 894 days.

(21) Appl. No.: 12/009,957

(22) Filed: Jan. 22, 2008

(65) Prior Publication Data

US 2008/0255536 A1    Oct. 16, 2008

Related U.S. Application Data

(60) Provisional application No. 60/881,861, filed on Jan. 23, 2007.

(51) Int. Cl.
*A61M 31/00* (2006.01)
*A61C 5/14* (2006.01)
*A61C 19/06* (2006.01)

(52) U.S. Cl.
CPC .. *A61C 19/06* (2013.01); *A61C 5/14* (2013.01)
USPC .............. 604/514; 604/77; 433/24; 433/80; 433/87; 433/88

(58) Field of Classification Search
USPC .............. 604/500, 77; 128/869, 847; 433/88
See application file for complete search history.

(56) References Cited

U.S. PATENT DOCUMENTS

| | | | | |
|---|---|---|---|---|
| 1,646,942 A | * | 10/1927 | Tuorto | 433/88 |
| 3,747,595 A | * | 7/1973 | Grossan | 601/160 |
| 6,152,733 A | * | 11/2000 | Hegemann et al. | 433/80 |
| 6,536,423 B2 | * | 3/2003 | Conway | 128/200.14 |
| 7,544,204 B2 | * | 6/2009 | Krespi et al. | 607/88 |
| 2006/0047329 A1 | * | 3/2006 | Krespi et al. | 607/86 |
| 2007/0299396 A1 | * | 12/2007 | Rocklin | 604/131 |
| 2008/0155771 A1 | * | 7/2008 | Agbaje | 15/23 |

OTHER PUBLICATIONS

Hydro Med; Grossan Hydro Pulse™ Quick Instructions; http://www.hydromedonline.com/hydropulse_shortdirections.html; Jan. 20, 2008; 2 pages.
Hydro Med; The Grossan Hydro Pulse Sinus System; http://www.hydromedonline.com/hp.html?referrer=GoogleG3a9 &gclid=CKj194jAhZECFSdZiAod0HmA-g; Jan. 20, 2008; 4 pages.

* cited by examiner

*Primary Examiner* — Kami A Bosworth
*Assistant Examiner* — Imani Hayman
(74) *Attorney, Agent, or Firm* — Peloquin, PLLC; Mark S. Peloquin (57) ABSTRACT

Methods and apparatuses include applying a biting force to a bite-piece, the biting force is applied by a user's teeth, wherein the bite-piece is held inside of the user's mouth. Closing the mouth and the biting force suppress the user's gag reflex and the user's tonsils and adjacent Throat structures can be treated by spraying fluid onto the tonsil or manipulating the surface of the tonsil and related structures. The tonsils can be cleaned thereby.

6 Claims, 12 Drawing Sheets

METHODS AND APPARATUSES FOR
TREATING TONSILS

This application claims priority to U.S. Provisional Patent Application No. 60/881,861 entitled "Tonsillith Cleaner," filed on Jan. 23, 2007. U.S. Provisional Patent Application No. 60/881,861 entitled "Tonsillith Cleaner," is hereby fully incorporated by reference.

BACKGROUND OF THE INVENTION

1. Field of Invention

Embodiments of the invention relate generally to mouth and throat hygiene, and more specifically, to apparatuses and methods used to cleanse the tonsils and upper throat areas of a mouth.

2. Background

During the normal course of life, food particles can collect in a person's mouth during the process of chewing and swallowing food. These food particles collect around the teeth and the person can remove them to some degree by brushing and flossing the teeth. Some of these food particles can become caught in the folds and fissures or crypts of the tonsils and are not removed during normal teeth hygiene, i.e., brushing and flossing teeth. Mucous and saliva, as well as tissue sloughed from the tonsil itself, can also become caught in the fissures or crypts of the tonsils.

All of these deposits; food, mucous, saliva, etc., generally referred to herein as "debris," can remain lodged in the structures of the tonsils and can present sites for bacteria to grow. This condition is undesirable; it can contribute to Halitosis and can present a problem to the person's health.

Tonsil and throat tissue are very sensitive to touch and the area of the mouth that includes the back of the throat where the tonsils are located is protected from invasion by foreign objects through the body's "gag" reflex. The gag reflex can present a problem to cleansing this area.

Medical evidence suggests that cleaning tonsils may reduce the rate of recurrent tonsillitis. However, it is often difficult for a person to locate the tonsils. A person's gag reflex makes insertion of washing instrumentation difficult. This can present a problem.

A commercially available product, the Grossan Hydro Pulse® System, which is designed to clean the back of the Tongue and tonsils, can stimulate the gag reflex in people when used to clean the back of the Tongue, the rear Throat areas, and the tonsils. This can present a problem.

BRIEF DESCRIPTION OF THE DRAWINGS

The invention may best be understood by referring to the following description and accompanying drawings that are used to illustrate embodiments of the invention. The invention is illustrated by way of example in the embodiments and is not limited in the figures of the accompanying drawings in which like references indicate similar elements.

DETAILED DESCRIPTION

In the following detailed description of embodiments of the invention, reference is made to the accompanying drawings in which like references indicate similar elements and in which are shown by way of illustrations, specific embodiments in which the invention may be practiced. These embodiments are described in sufficient detail to enable those of skill in the art to practice the invention. In other instances, well-known circuits, structures, and techniques have not been shown in detail in order not to obscure the understanding of this description. The following detailed description is, therefore, not to be taken in a limiting sense and the scope of the invention is defined only by the appended claims.

Apparatuses and methods are described that allow a person to locate and treat his or her tonsils by significantly suppressing the "gag" reflex. Treating tonsils, as taught by embodiments of the invention, includes but is not limited to, washing debris from the folds and crypts or fissures that exist within the tonsils and associated structures. "Debris" as used in this description of embodiments includes, food, mucous, saliva, etc., that is any material that comes into contact with and clings to a tonsil. Treating also includes, but is not limited to, rubbing and touching the tonsil and delivering fluid to the surface of the tonsil. Fluids include but are not limited to water, saline solution, antiseptic solution, etc.

Figure 1A:
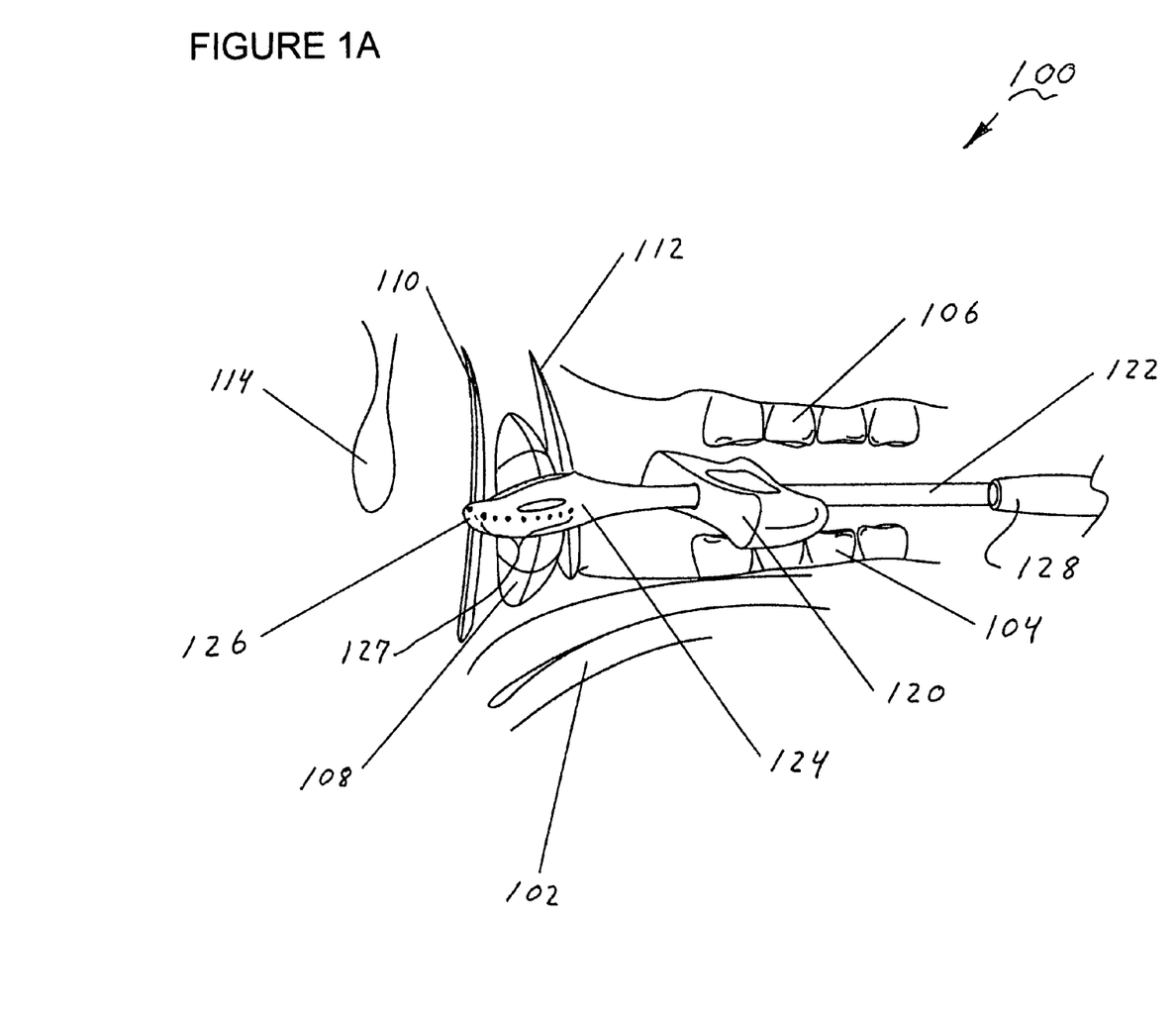
FIG. 1A illustrates a side view of an apparatus for treating a tonsil(s) according to one embodiment of the invention.
Figure 1B:
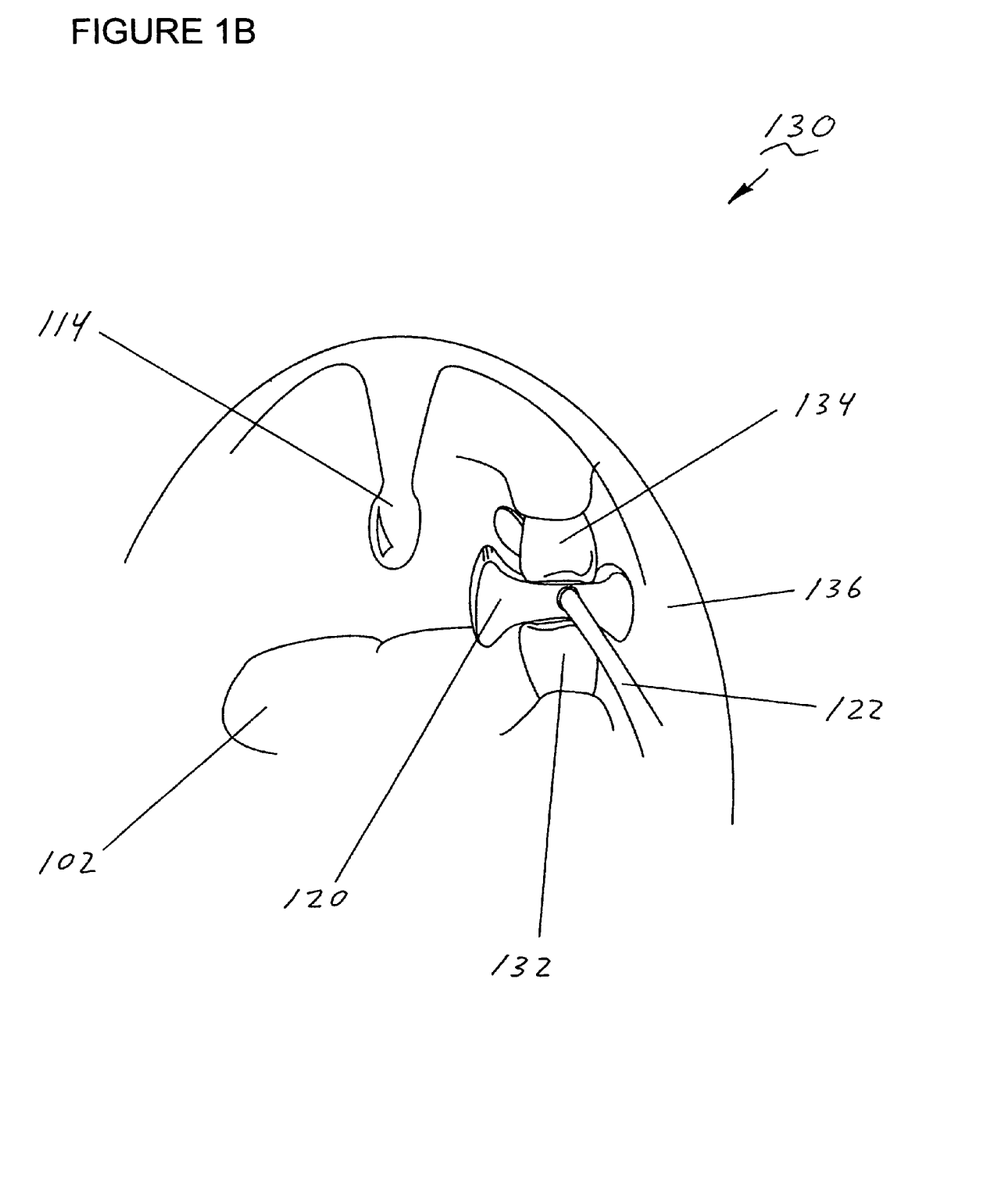
FIG. 1B illustrates a front view of the apparatus from FIG. 1A.
Figure 1C:
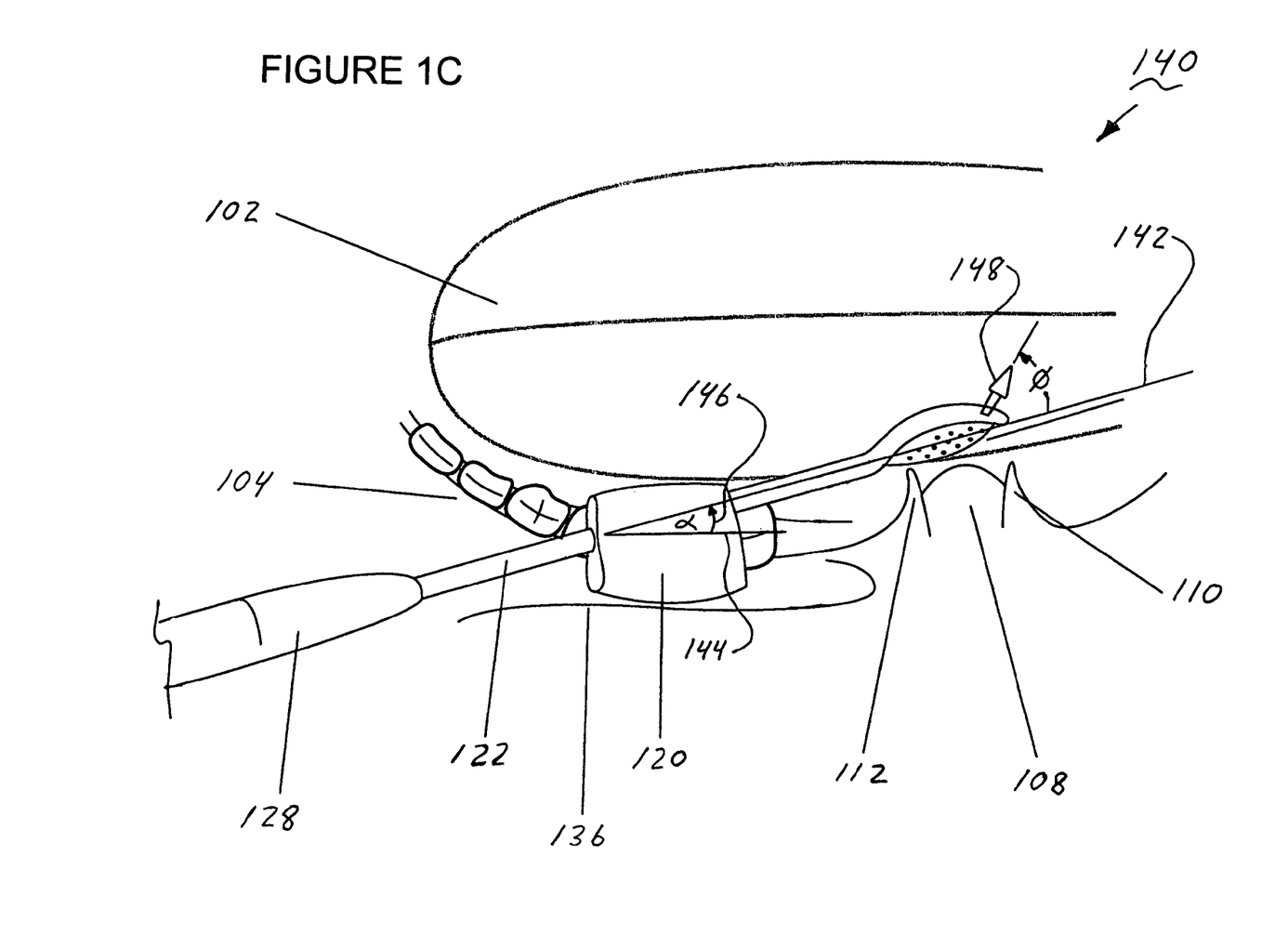
FIG. 1C illustrates a top view of the apparatus from FIG. 1A.

FIG. 1A illustrates, generally at 100, an apparatus for treating a person's tonsil(s) according to one embodiment of the invention, in a side view of a mouth. FIG. 1B illustrates in a front view of the mouth, the apparatus from FIG. 1A. FIG. 1C illustrates in a top view of mouth, the apparatus from FIG. 1A. Referring now to FIGS. 1A, 1B, and 1C collectively, the mouth has a Tongue 102, Teeth 104 populate a Lower Jaw and Teeth 106 populate an Upper Jaw. The left side of the mouth has a tonsil 108, framed by a Back Pillar 110 and a Front Pillar 112. A Uvula 114 is shown extending down from above the Tongue 102.

The apparatus has a fluid delivery tube 122, which is slidingly engaged with a bite-piece 120. The fluid delivery tube 122 has a first end, which is designed to be grasped by a person (user) in the vicinity of the forward part of a handle 128. The handle 128 is a built over the fluid delivery tube 122. The fluid delivery tube 122 has a second end, which is in the form of a fluid delivery head 124. The fluid delivery head 124 terminates in a bumper 126. The bumper 126 as well as the fluid delivery tube 122 and fluid delivery head 124 are designed to present rounded surfaces to the user's mouth and are free of sharp edges.

A user inserts the apparatus into his or her mouth into the position illustrated in FIG. 1A. The user closes the mouth so that the lower teeth 104 and the upper teeth 106 apply biting pressure to the bite-piece 120. With reference to FIG. 1B, a lower tooth 132 and an upper tooth 134 apply biting pressure to the bite-piece 120, as illustrated generally at 130. An inside surface of the user's left cheek 136 is indicated in FIG. 1B for clarity of illustration.

The apparatus has been designed to suppress the user's gag reflex. It was discovered that when the mouth is closed user applies biting pressure to the bite-piece; the user's gag reflex is suppressed thereby in the same manner as it is suppressed when chewing and swallowing food. Suppression of the gag reflex permits the tonsil and surrounding areas (structures) to be manipulated by the apparatus thereby facilitating the removal of debris by washing, deflecting, rubbing, etc. the surface of the tonsil, which includes the folds and fissures or crypts in which debris can collect.

According to one embodiment of the invention, an example of manipulation is washing or showering the tonsil with fluid that flows through the fluid delivery tube 122 and out of the fluid delivery head 124. As illustrated, generally at 140, in FIG. 1C, the fluid delivery head 124 has a plurality of holes, which permits fluid to shower the tonsil 108, Forward Pillar 112, Back Pillar 110 and the crypts or fissures contained therein. Such showering can dislodge and wash debris from these structures. The fluid flows through the fluid delivery tube 122, out of the fluid delivery head 124, showers the tonsil 108 and related structures of the throat while the user is clenching the bite-piece 120 in the user's teeth, e.g., 132 and 134.

In another embodiment of the invention, the fluid delivery head 124 is configured to spray fluid onto both a right and a left tonsil at substantially the same time. Such a configuration is achieved by providing holes for water to exit the fluid delivery head 124 on opposing sides of the head. An array of such holes is shown at 127, which are used in some embodiments to spray fluid onto a right tonsil and associated structures. In such a configuration, a valve can be included in the handle 128 to regulate the flow of fluid to the right tonsil. Individual fluid lines can be provided inside of the fluid delivery tube 122 to provide a higher pressure to the fluid exiting from holes 127 because of the greater distance that the fluid travels in order to reach the right tonsil relative to the distance that the fluid travels to reach the left tonsil.

The bite-piece 120 is slidingly engaged with the fluid delivery tube 122, such that the fluid delivery tube 122 can translate relative to the bite-piece 120 and rotate relative to the bite-piece 120. Such a configuration permits the user to manipulate the greater area of the tonsil 108 and surrounding structures (Forward Pillar 112 and Rear Pillar 110) as well as the area including the back of the throat and the roof of the mouth with a spray of fluid or to deflect the surfaces of these structures.

According to another embodiment of the invention, another example of manipulation is contacting the surface of the tonsil 108, Forward Pillar 112, Back Pillar 110, etc. with an attachment 148 placed into the fluid delivery head 124. In this example, the user rotates the fluid delivery tube 122 about its longitudinal axis 142 approximately one hundred and eighty degrees (180) to bring the attachment 148 into contact with the tonsil 108, and/or Front Pillar 112 and/or Back Pillar 110, etc. A variety of attachments 148 are described below in conjunction with FIG. 6 for use in this situation.

Embodiments of the invention are used to place the fluid delivery head 124 proximate to the tonsil 108. In one embodiment, the user's molars clench the bite-piece 120. The bite-piece is positioned on the molars with its longitudinal axis coincident with a tooth-line 144. The fluid delivery tube 122 is aligned at an angle $\alpha$ 146 relative to the longitudinal axis of the bite-piece and the tooth-line 144. Such alignment places the fluid delivery head 124 proximate to the tonsil 108 and related structures. The user is capable of "finding" the tonsil 108, i.e., spraying fluid or touching the surfaces (attachment 148) with the user's mouth closed.

Figure 1D:
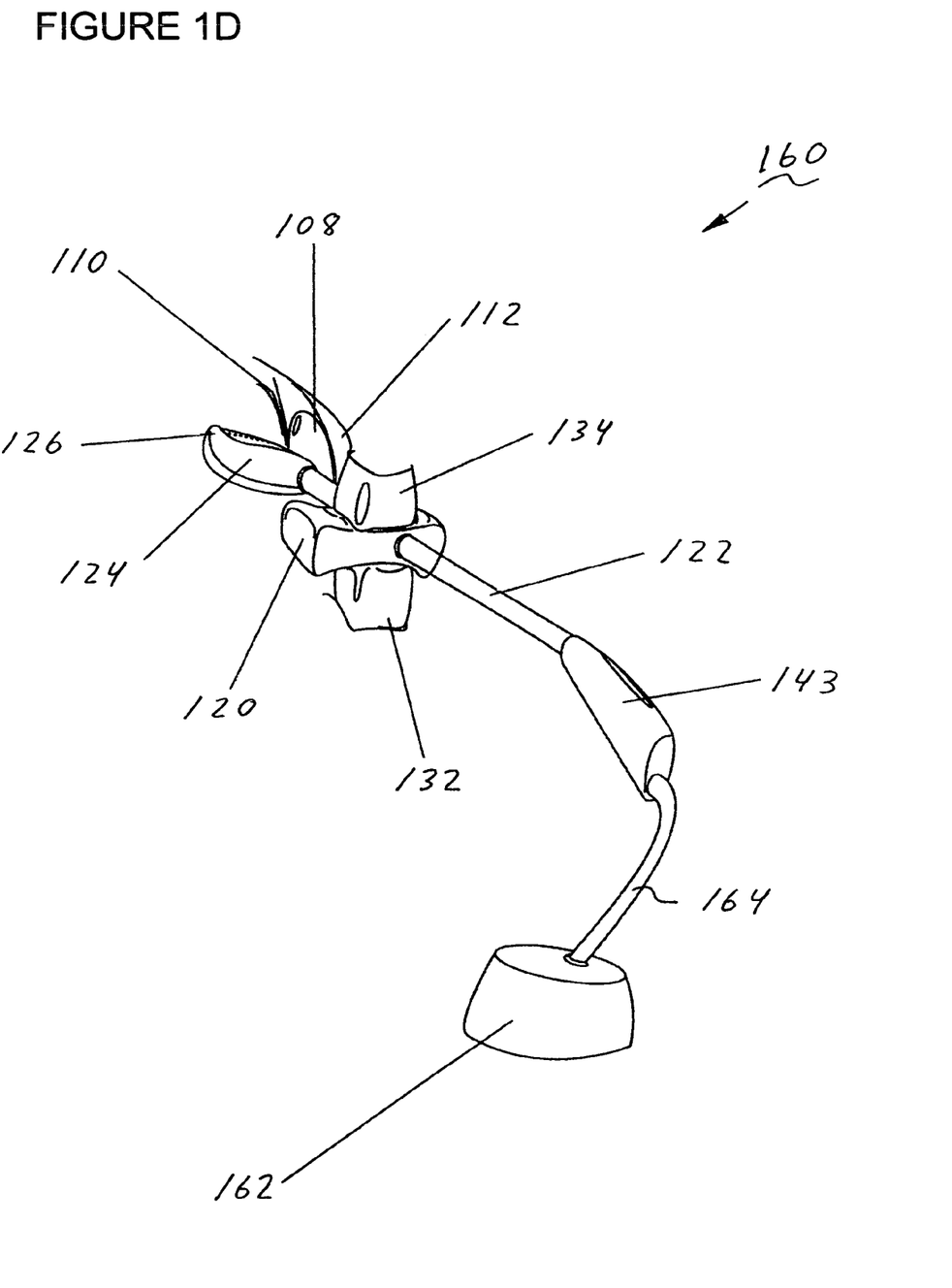
FIG. 1D illustrates a system according to the apparatus from FIG. 1A.

FIG. 1D illustrates, generally at 160, a system according to the apparatus of FIG. 1A. With reference to FIG. 1D, a source of pressurized fluid 162 is connected to the fluid delivery tube 122 by a flexible hose 164. A handle 143 is incorporated over the fluid delivery tube 122/flexible tube 164 such that the user can easily move (rotate and translate) the fluid delivery head 124. Such movement directs a shower of fluid over the area of interest in and around the tonsil 108, Forward Pillar 112, and Rear Pillar 110, and associated other areas of the throat, Tongue 102, etc. (related structures).

Figure 2:
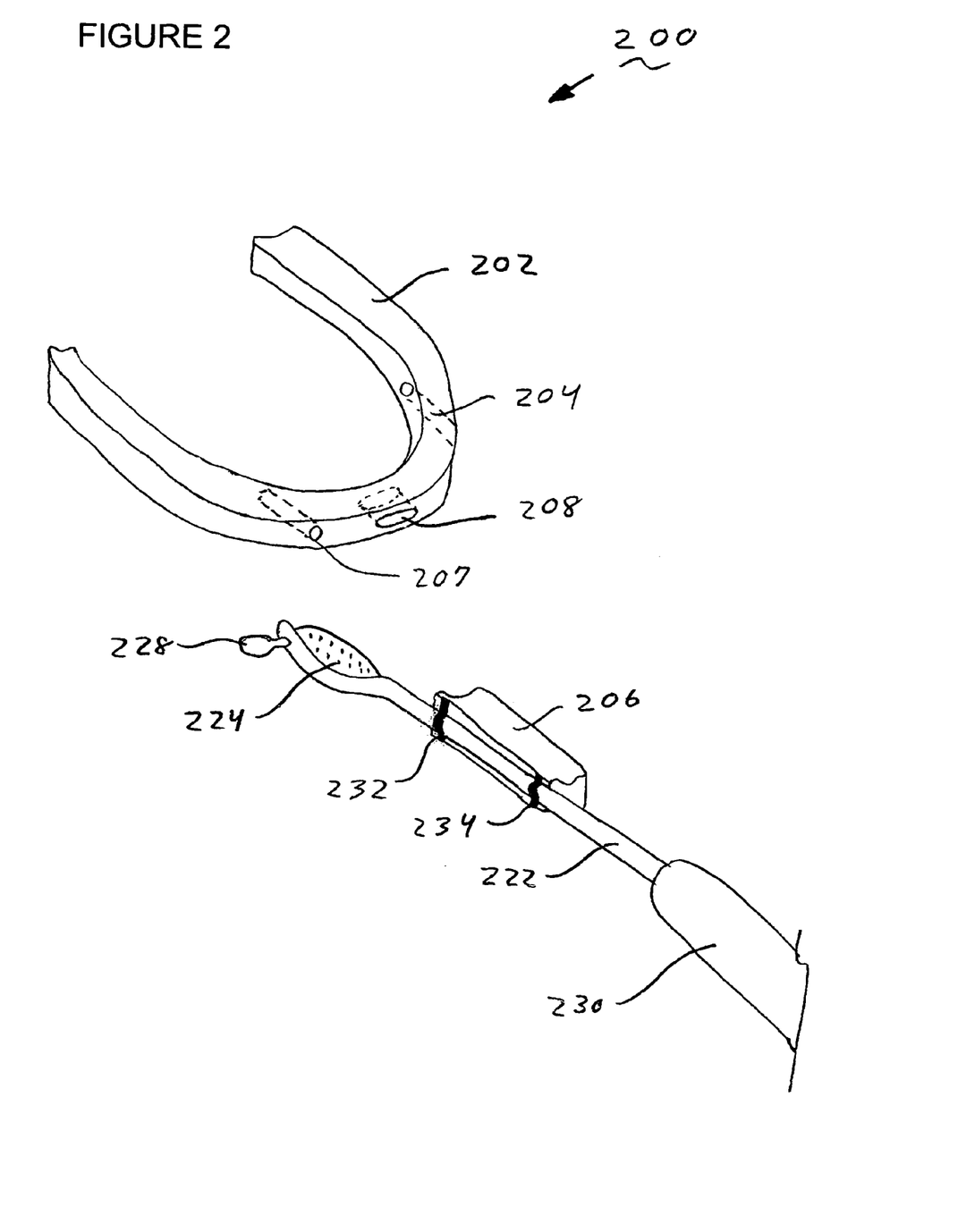
FIG. 2 shows various bite-pieces according to embodiments of the invention.

FIG. 2 illustrates, generally at 200, various bite-pieces according to embodiments of the invention. In general, bite-pieces can be of different designs and are not limited to a short length that spans only one, two, or three teeth. In one embodiment, a bite piece extends around and makes contact with a user's full set of teeth and with reference to FIG. 2, such a bite-piece is illustrated at 202. An alignment hole 204 is provided, through which a fluid delivery tube (not shown) can pass to position a fluid delivery head proximate to a user's left tonsil as illustrated in the previous figures. The bite-piece 202 can be flipped over one hundred and eighty (180) degrees to allow alignment between a fluid delivery head and a user's right tonsil. Alternatively, a second alignment hole 207 can be provided to permit a fluid delivery tube to pass therethrough and be located proximate to the user's right tonsil.

As fluid flows through the apparatus and showers a user's tonsils, Pillars, Throat, Tongue, etc. (throat structures) the fluid drains out of the user's mouth and into a receptacle such as a sink, bowl, etc. The bite-piece 202 can be provided with one or more drain holes 208 to facilitate the exit of the sprayed fluid from the user's mouth.

Alternatively, in some embodiments a suction tube is provided to remove sprayed fluid and debris from the user's mouth.

A bite-piece 206 is slidingly engaged with a fluid delivery tube 222 by means of tabs 232 and 234. In this embodiment, the fluid delivery tube 222 can both translate and rotate relative to the bite-piece 206. A handle 230, positioned exterior to the user's mouth is grasped by the user and is moved to place the fluid delivery head 224 proximate to the tonsils, etc. (not shown). Alternatively, the user can rotate the handle 230 one hundred and eighty degrees (180) to bring an attachment 228 (if installed) into contact with a tonsil, a Front Pillar, a Back Pillar, and related structures. The attachments to the fluid delivery head are described more fully below in conjunction with FIG. 6.

Figure 3:
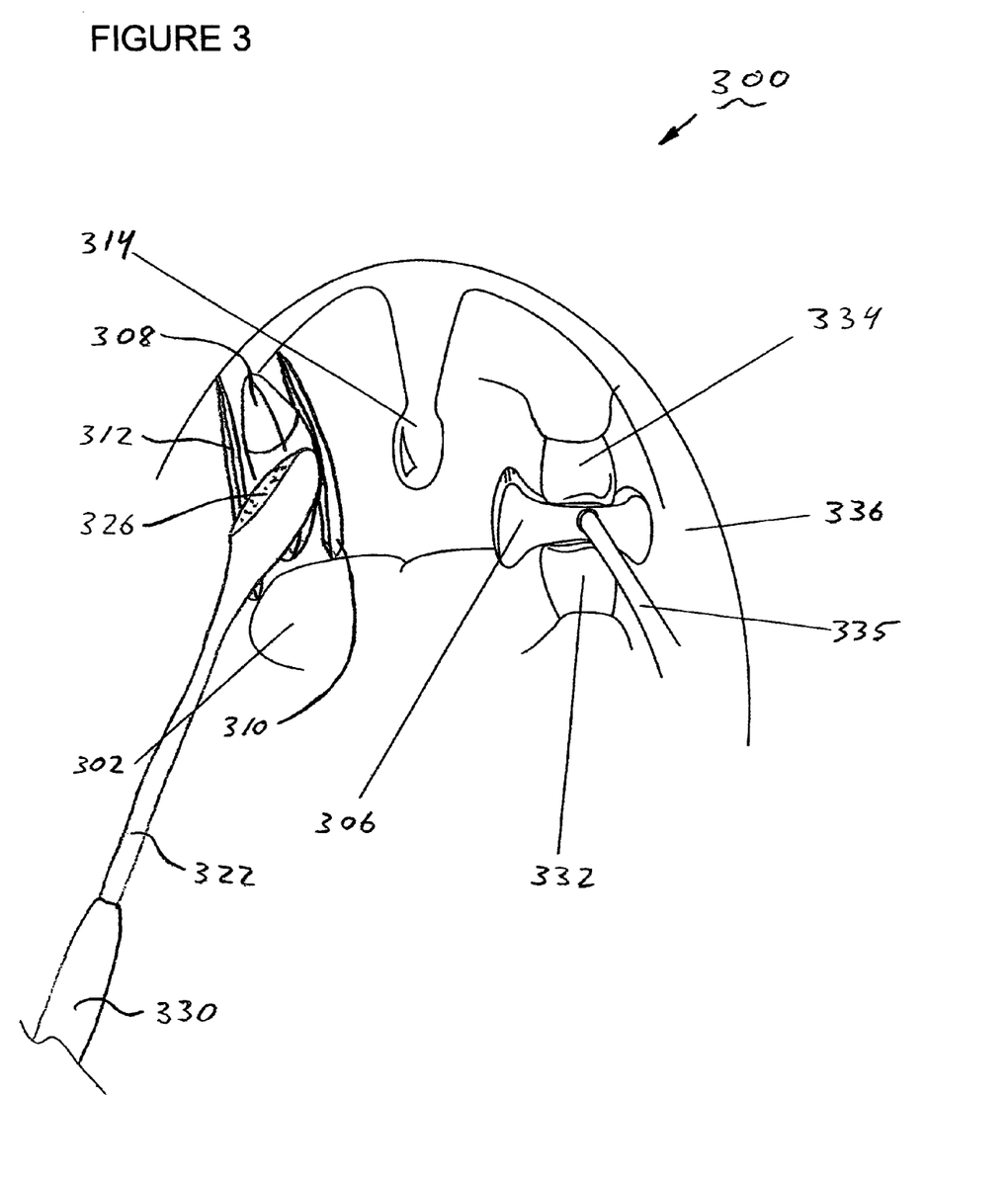
FIG. 3 illustrates a front view of an apparatus for treating a tonsil(s) according to embodiments of the invention.

FIG. 3 illustrates, generally at 300, a front view of an apparatus for treating a tonsil(s) according to embodiments of the invention. With reference to FIG. 3, a bite-piece 306 is separate from a fluid delivery tube 322. In the embodiment illustrated in FIG. 3, the user clenches the bite-piece 306 between the user's lower teeth (tooth) 332 and the user's upper teeth (tooth) 334. A rod 335, connected to the bite-piece 306, facilitates insertion and removal of the bite-piece 306. As the user clenches the bite-piece, the user's gag reflex is suppressed, thereby permitting treatment of a tonsil 308 (and surrounding structures) by flushing with fluid, deflection of the respective surfaces by swabbing, touching, rubbing, scrubbing, etc.

A user's left cheek is indicated at 336, the user's tongue at 302, and a Uvula at 314. The right tonsil 308 is framed by a Front Pillar 312 and a Back Pillar 310. A handle 330 is connected to a fluid delivery tube 322. The fluid delivery tube 322 is connected to a fluid delivery head 326. As described above in conjunction with the previous figures, the user directs a flow of fluid onto the tonsil 308 and/or surrounding structures 312, 310, etc. by moving the handle which is located outside of the user's mouth. The fluid delivery tube 322 is supplied with a flow of fluid.

As described above, embodiments of the invention allow a user to treat the tonsils with the user's mouth closed. Thus, in various embodiments, the apparatus provides a locating function in which the fluid delivery head is placed proximate to the tonsil and the surrounding structures, e.g., Front Pillar, Back Pillar, etc. through placement of the apparatus into a user's mouth and location between the user's teeth.

Figure 4:
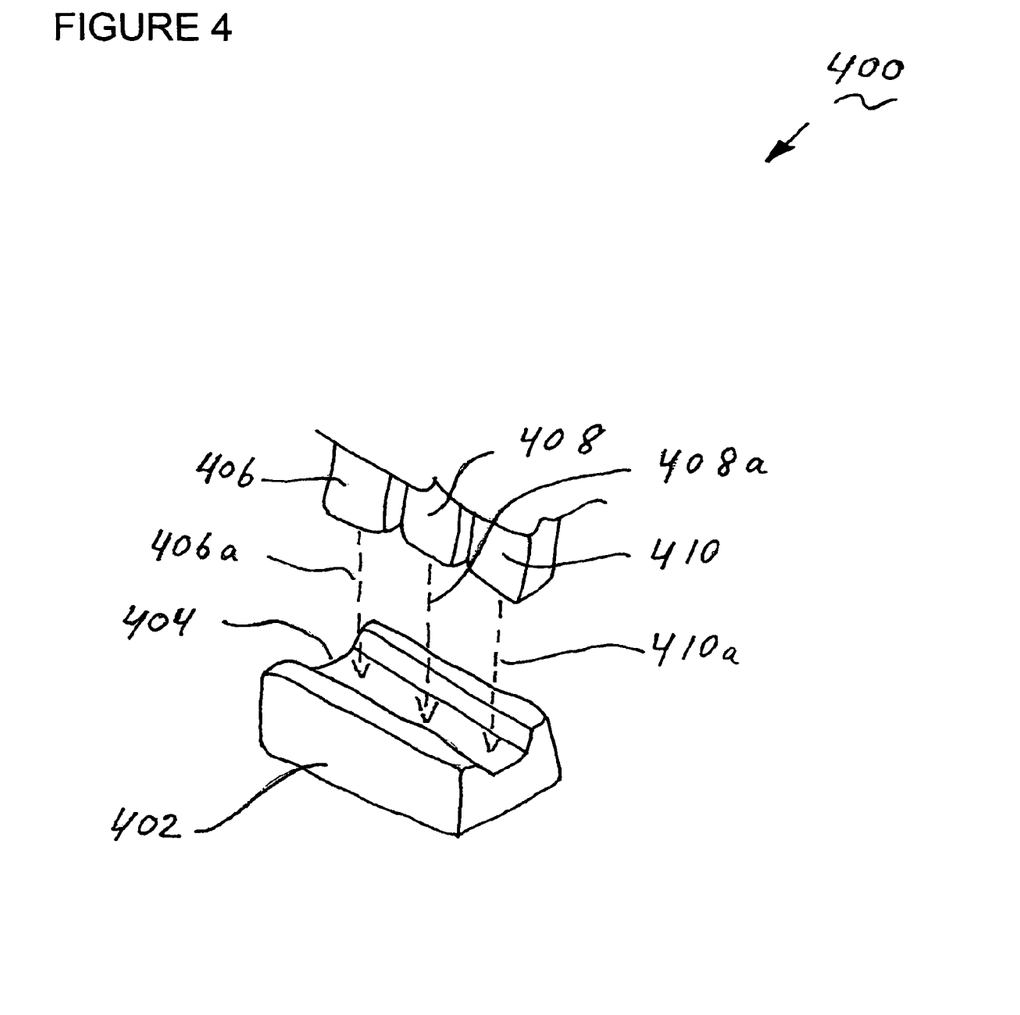
FIG. 4 illustrates a bite-piece with an alignment groove according to one embodiment of the invention.

FIG. 4 illustrates, generally at 400, a bite-piece with an alignment groove according to one embodiment of the invention. With reference to FIG. 4, a bite-piece 402 has an alignment groove (track) 404 impressed therein. When a user clenches his or her teeth 406, 408, and 410, the teeth (406, 408, and 410) move as indicated by direction arrows 406a, 408a, and 410a placing the teeth into contact with the bite-piece 402. As the teeth 406, 408, and 410 move into the alignment track 404, a longitudinal axis of the bite-piece 402 becomes coincident with a tooth-line as illustrated in FIG. 1C at 144. As illustrated in FIG. 4, alignment with the rear molars is preferred in one embodiment and such alignment is illustrated in FIG. 1A and FIG. 1C.

Figure 5:
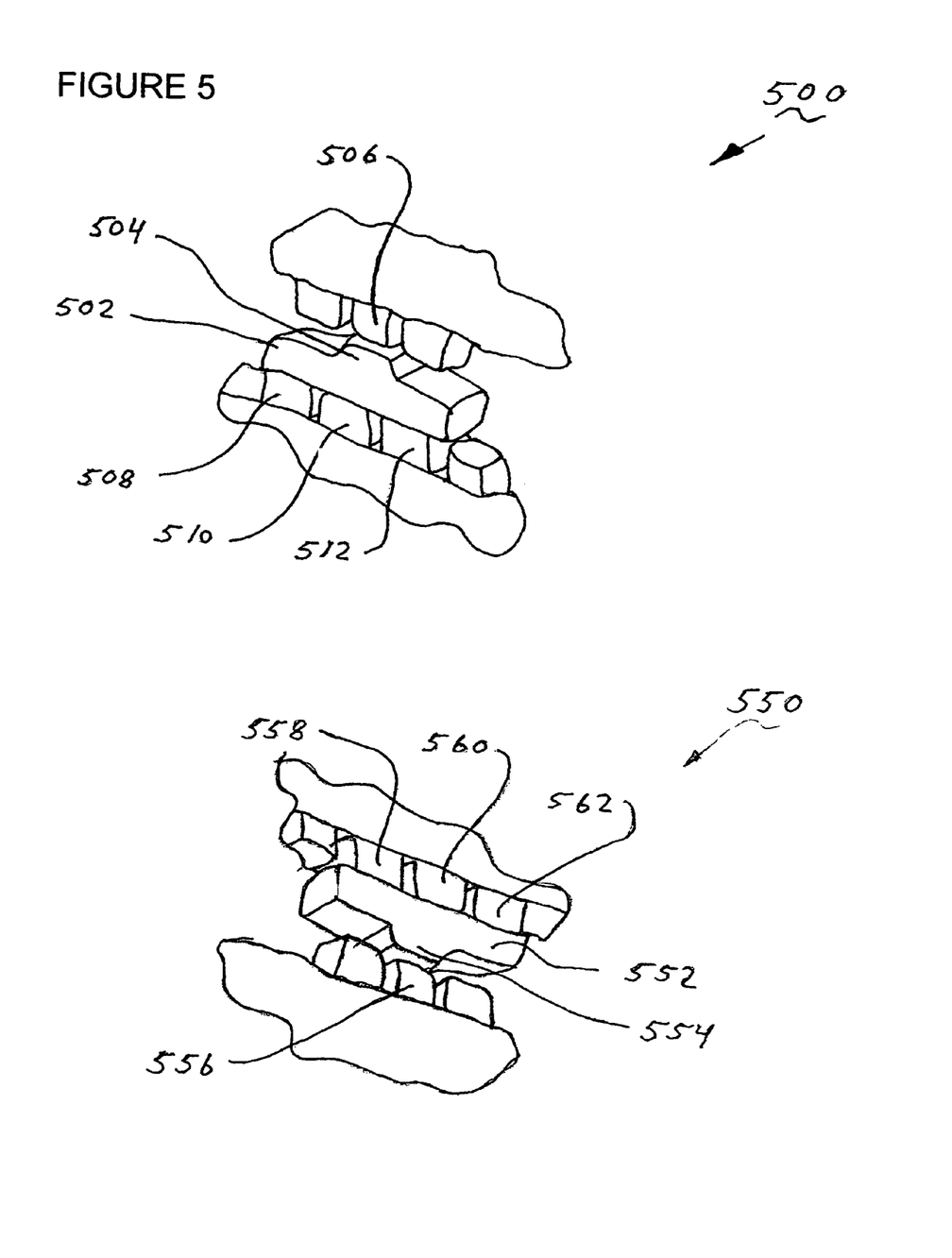
FIG. 5 depicts bite-pieces according to embodiments of the invention.

FIG. 5 depicts bite-pieces according to embodiments of the invention. With reference to FIG. 5 and 500, a bite piece is illustrated at 502. The bite piece 502 is designed to contact several lower teeth, i.e., 508, 510, and 512 and one upper tooth 506. The upper tooth 506 contacts a raised portion 504 of the bite-piece 502. Clenched between a user's teeth as illustrated in 500 the bite-piece provides a platform that is used to align a fluid delivery tube as illustrated in the previous figures. Such a design can be useful when it is desirable to obtain alignment from a lower row of teeth and to remove contact from particular upper teeth.

With reference to 550 in FIG. 5, a bite piece 552 is illustrated in contact with upper teeth 558, 560, and 562 on the upper surface of the bite-piece. The bite piece 552 is designed to contact several upper teeth, i.e., 558, 560, and 562 and one lower tooth 556. The lower tooth 556 contacts a raised portion 554 of the bite-piece 552. Clenched between a user's teeth as illustrated in 550, the bite-piece provides a platform that is used to align a fluid delivery tube as illustrated in the previous figures. Such a design can be useful when it is desirable to obtain alignment from an upper row of teeth and to remove contact from particular lower teeth.

Figure 6:
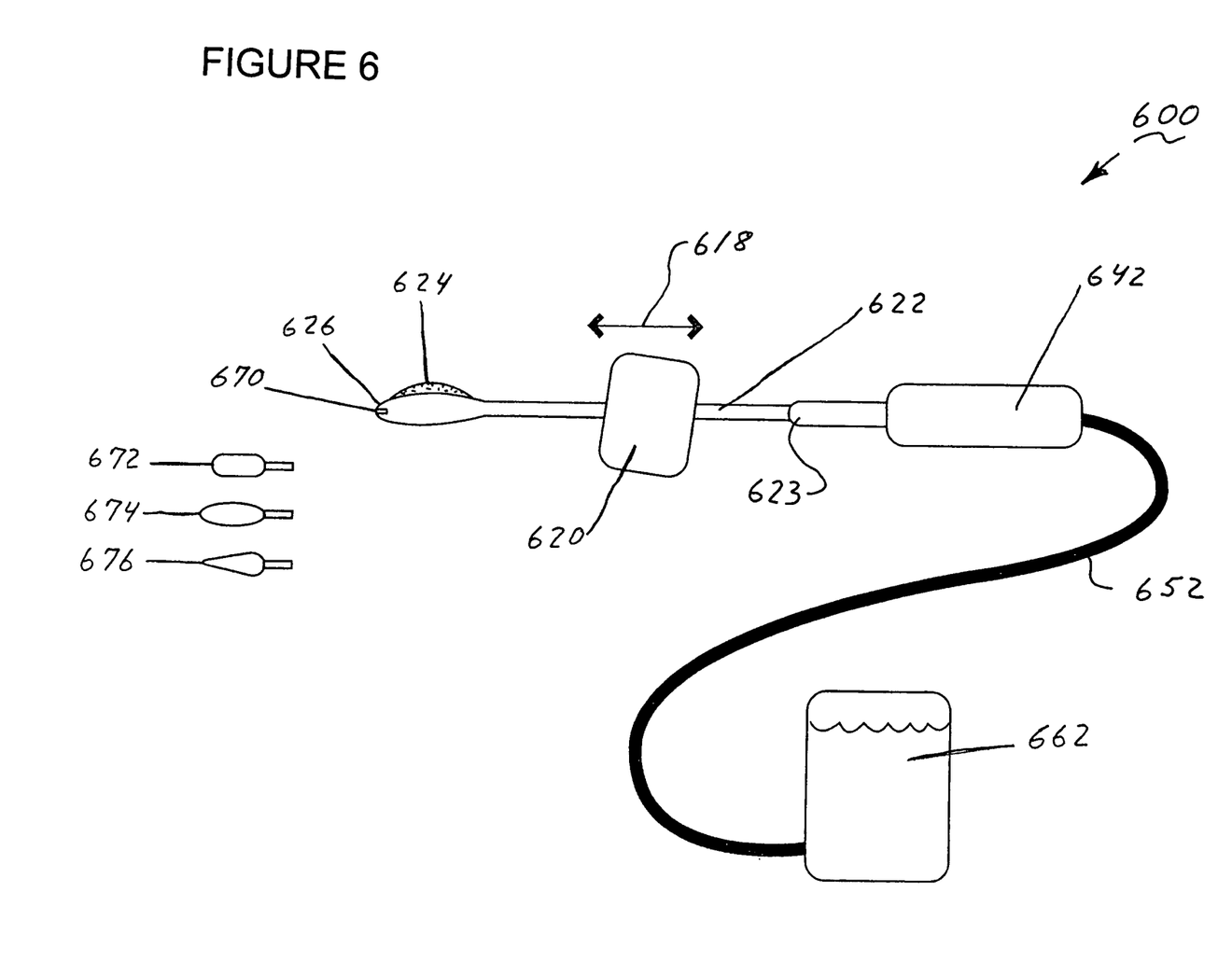
FIG. 6 illustrates a system for treating a tonsil(s) according to embodiments of the invention.

FIG. 6 illustrates, generally at 600, a system for treating a person's tonsil(s) according to embodiments of the invention. With reference to FIG. 6, the system includes a fluid reservoir 662 containing a supply of fluid. A flexible tube 652 connects the fluid reservoir 662 to a fluid delivery tube 622. A handle 642 enlarges the diameter of the fluid delivery tube 622 to provide a surface with which a user can move a fluid delivery head 624 proximate to a tonsil and other structures of interest as described above. The fluid delivery tube 622 can translate relative to a bite-piece 620 as indicated by an arrow 618.

A diameter of the fluid delivery tube 622 increases at a point 623 to provide a limit on the translation of the fluid delivery tube 622 relative to the bite-piece 618. Limiting the translation of the fluid delivery tube 622 helps to keep the fluid delivery head 624 proximate to the user's tonsil and other structures of interest.

The fluid delivery head 624 terminates in a bumper 626. The bumper 626 and the fluid delivery head 624 have rounded surfaces without sharp angles. This is done to minimize any choking sensation and to help further suppress the gag reflex.

The end of the fluid delivery head 624 has a location 670 configured to receive an attachment such as a brush attachment 672, a swab attachment 674, and a rubber attachment 676. Attachments are used in various embodiments to manipulate the surface of the tonsil, Front Pillar, Rear Pillar, throat area, etc. as described above.

Figure 7:
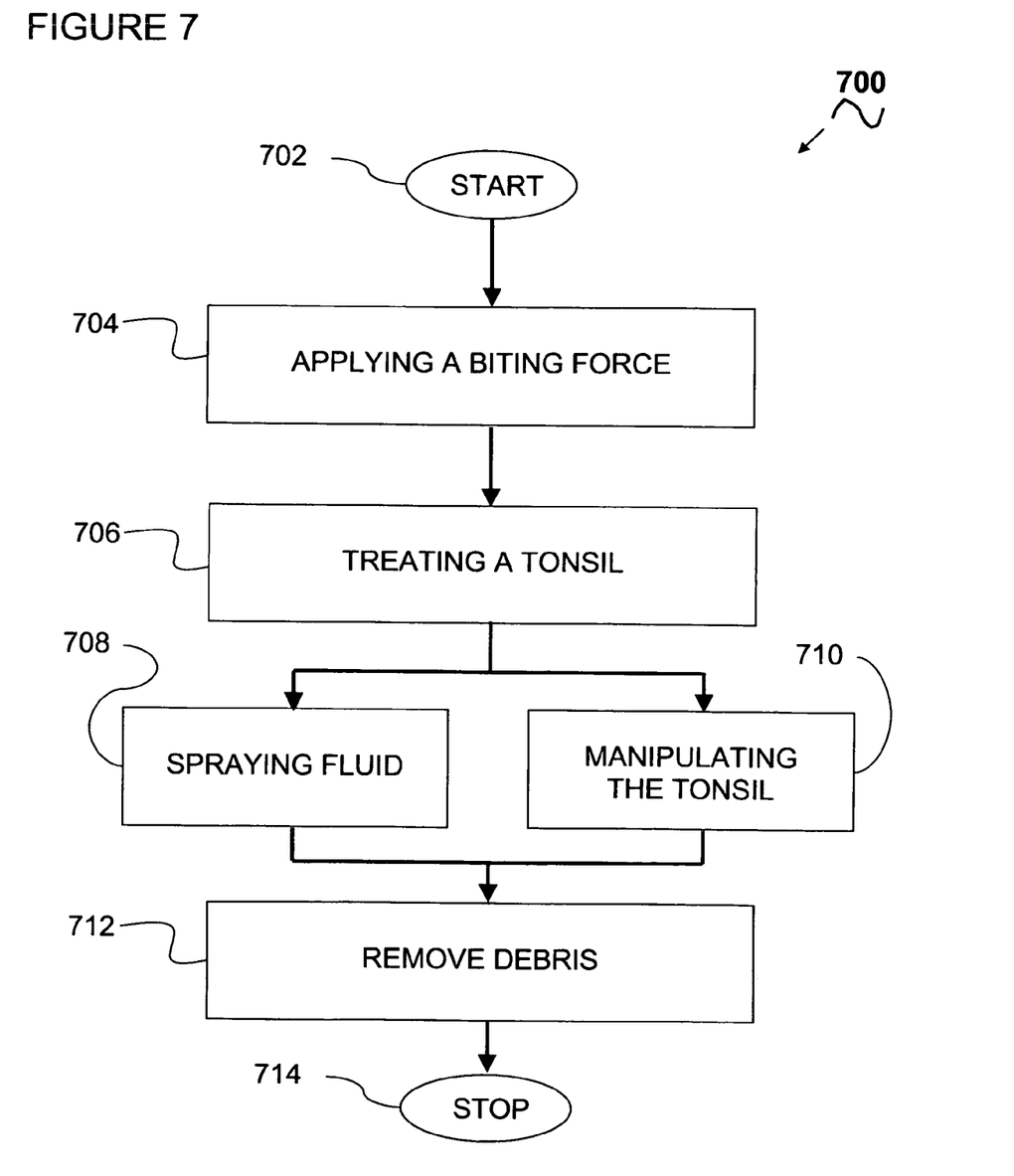
FIG. 7 illustrates methods for treating a tonsil and/or related structures.

FIG. 7 illustrates, generally at 700, processes for treating a tonsil and/or related structures. With reference to FIG. 7, a method commences at a block 702. At a block 704, a user applies a biting force to a bite-piece, clenching the bite-piece in the user's teeth. The biting force suppresses a gag reflex in the user. At a block 706, the user's tonsil and/or related structures are treated. Related structures include, but are not limited to, a tonsil(s), a front Pillar(s), a Rear Pillar(s), the Throat, the Tongue, etc. Fluid is sprayed on the tonsil and/or related structures at a block 708. A tonsil and/or related structures are manipulated at a block 710. At a block 712 debris is removed from the tonsil and/or related structures. The process ends at a block 714.

Figure 8:
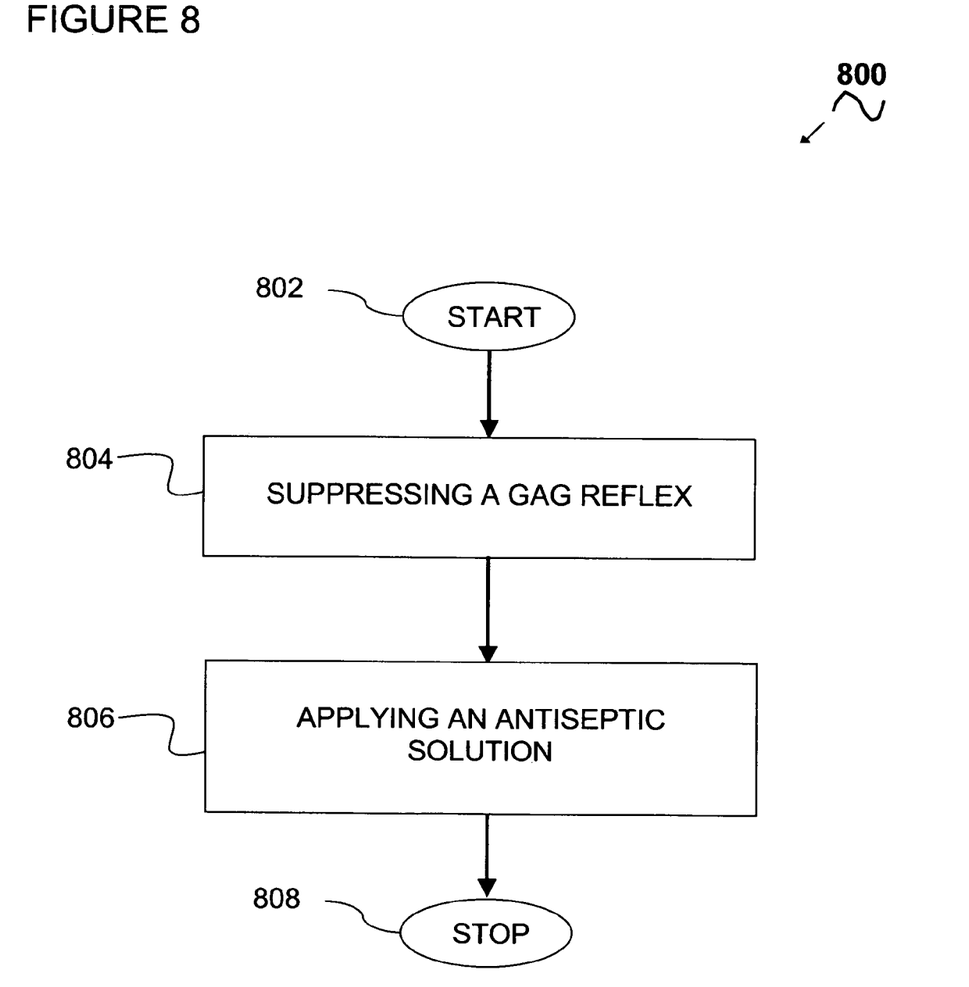
FIG. 8 illustrates a method for combating Tonsillitis.

FIG. 8 illustrates, generally at 800, a process for combating Tonsillitis. With reference to FIG. 8, a process commences at a block 802. At a block 804, the gag reflex in a person is suppressed. At a block 806, the user applies an antiseptic solution to his or her tonsils. The process at the block 806 is repeated once a day for approximately two weeks. Medical evidence suggests that cleaning tonsils may reduce the rate of recurrent Tonsillitis. The process ends at a block 808.

Figure 9:
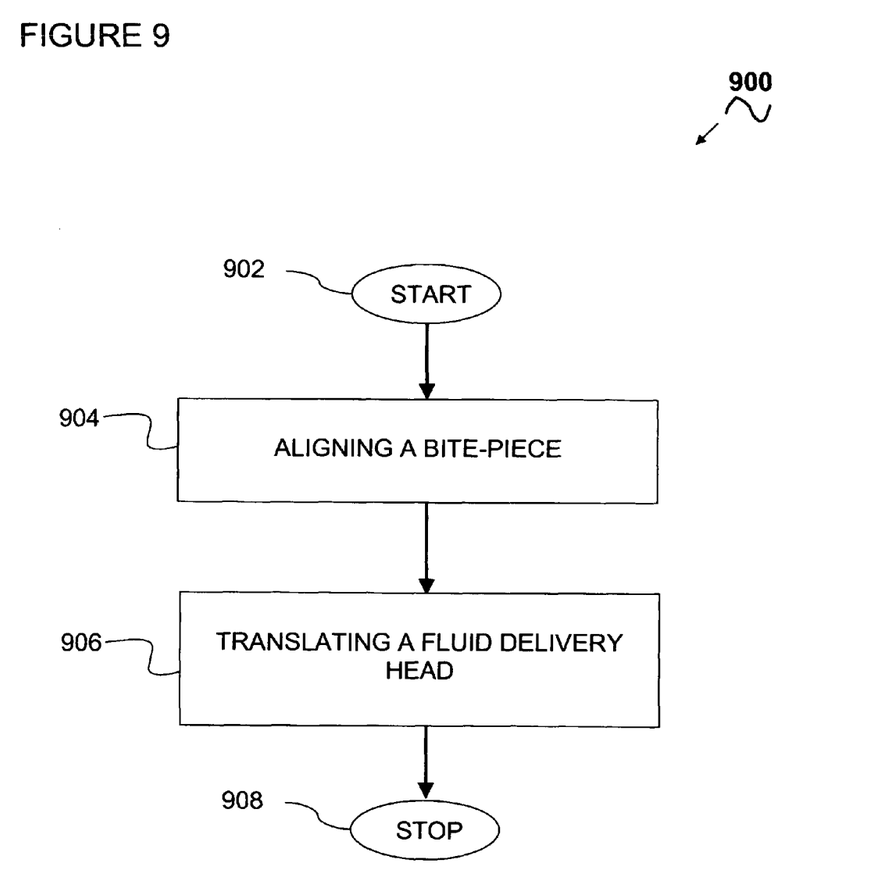
FIG. 9 illustrates, generally at 900, locating a fluid delivery head proximate to a tonsil.

FIG. 9 illustrates, generally at 900, locating a fluid delivery head proximate to a tonsil. With reference to FIG. 9, a process commences at a block 902. At a block 904, a bite-piece is aligned with a user's teeth. At a block 906, a fluid delivery head is translated relative to the bite-piece until the fluid delivery head is proximate to the tonsil. The process ends at a block 908.

For purposes of discussing and understanding embodiments of the invention described herein, it is to be understood that various terms are used by those knowledgeable in the art to describe techniques and approaches.

Furthermore, in this description, for purposes of explanation, numerous specific details are set forth in order to provide a thorough understanding of the embodiments of the invention presented. It will be evident, however, to one of ordinary skill in the art that embodiments of the invention may be practiced without these specific details. In some instances, well-known structures and devices are shown in block diagram form, rather than in detail, in order to avoid obscuring embodiments of the invention. These embodiments are described in sufficient detail to enable those of ordinary skill in the art to practice the invention, and it is to be understood that other embodiments may be utilized and that logical, mechanical, electrical, and other changes may be made without departing from the scope of the embodiments of the invention described.

As used in this description, "one embodiment" or "an embodiment" or similar phrases mean that the feature(s) being described is included in at least one embodiment of the invention. References to "one embodiment" in this description do not necessarily refer to the same embodiment; however, neither are such embodiments mutually exclusive. Nor does "one embodiment" imply that there is but a single embodiment of the invention. For example, a feature, structure, act, etc. described in "one embodiment" may also be included in other embodiments. Thus, the invention may include a variety of combinations and/or integrations of the embodiments described herein.

While the invention has been described in terms of several embodiments, those of skill in the art will recognize that the invention is not limited to the embodiments described, but can be practiced with modification and alteration within the spirit and scope of the appended claims. The description is thus to be regarded as illustrative instead of limiting.

What is claimed is:

1. A method comprising: suppressing a gag reflex in a user by providing a bite-piece which the user can apply a biting force to when the bite-piece is clenched between a user's teeth; and spraying fluid onto a user's tonsil using a fluid delivery tube during the suppressing, wherein sprayed fluid can wash debris from the user's tonsil.

2. The method of claim 1, further comprising:
   manipulating a direction of sprayed fluid during the spraying, such that the frontal area of the user's tonsil can be washed.

3. A method comprising:
   aligning a longitudinal axis of a bite-piece with a tooth-line of a person's teeth as the person's teeth apply biting force to the bite-piece; and
   translating a fluid delivery head relative to the bite-piece, wherein the bite-piece constrains linear motion of the fluid delivery head to one direction and the fluid delivery head is proximate to a person's tonsil when the translating stops, the fluid delivery head is connected to a fluid delivery tube.

4. The method of claim 3, wherein a track in the bite-piece engages with the person's teeth during the aligning.

5. The method of claim 4, wherein a person's molars are used during the aligning.

6. The method of claim 1, wherein the user's teeth are the user's molars on either the right or the left side of a user's mouth.

* * * * *